United States Patent [19]
Matthews et al.

[11] 4,397,644
[45] Aug. 9, 1983

[54] SANITARY NAPKIN WITH IMPROVED COMFORT

[75] Inventors: Billie J. Matthews, Menasha; John P. Allison, Appleton; Paul S. Woon, Appleton; Robert A. Stevens, Appleton; Stephan R. Bornslaeger, Appleton, all of Wis.

[73] Assignee: Kimberly-Clark Corporation, Neenah, Wis.

[21] Appl. No.: 345,888

[22] Filed: Feb. 4, 1982

[51] Int. Cl.³ .............................................. A61F 13/16
[52] U.S. Cl. .................................... 604/378; 604/370
[58] Field of Search ................. 604/370, 374, 378–380

[56] References Cited
U.S. PATENT DOCUMENTS

| | | | |
|---|---|---|---|
| 3,881,490 | 5/1975 | Whitehead et al. | 604/380 |
| 3,886,941 | 6/1975 | Duane et al. | 604/378 |
| 3,934,588 | 1/1976 | Mesek et al. | 604/378 |
| 4,055,180 | 10/1977 | Karami | 604/378 |
| 4,173,046 | 11/1979 | Gallagher | 604/378 |

Primary Examiner—C. Fred Rosenbaum
Attorney, Agent, or Firm—Howard Olevsky; R. Jonathan Peters; Gregory E. Croft

[57] ABSTRACT

A sanitary napkin is provided which is capable of transmitting viscous menstrual fluid into the absorbent portion of the napkin without cover runoff. The napkin has a fluid permeable cover which is integrated with a portion of the absorbent matrix. This portion of the absorbent matrix is also designed to provide increased comfort, initially during use, and after the napkin has become wet.

19 Claims, 4 Drawing Figures

SANITARY NAPKIN WITH IMPROVED COMFORT

FIELD OF THE INVENTION

This invention relates generally to sanitary napkins and particularly to a sanitary napkin featuring improved comfort and absorbency.

BACKGROUND OF THE INVENTION

Sanitary napkins are conventionally made of layers of cellulosic material such as wood pulp fluff, creped wadding or the like. These materials provide relatively good absorbency and some shape recovery when dry. Unfortunately, when these napkins are wet, the cellulosic material collapses, loses its shape and is much less comfortable to the wearer; with the result that even the low levels of shape recovery and flexibility present in the cellulosic material in the dry state tend to disappear.

Recognition of the discomfort problems associated with these napkins, both in the wet and dry form, has produced a variety of solutions. One of these solutions involves the addition of so-called super-absorbent materials to a sanitary napkin with the concomitant decrease in conventional cellulosic absorbents. This has resulted in a thin napkin which distorts easily and which suffers from loss of shape recovery.

Another solution which has been discussed in the patent literature involves the concept of adding thermoplastic material to the absorbent matrix. The thermoplastic is typically added as fibers or powder. It has been intermingled with the absorbent to keep the capillaries within the absorbent open, and at varying levels with decreased amounts present in the center or most absorbent area of the absorbent matrix. In the latter case, thermoplastic is added to establish a capillary gradient in which absorbent layers with larger capillaries are present nearest the body of the wearer.

Examples of the addition of thermoplastic can be found in: U.S. Pat. Nos. 4,082,886 and 4,129,132 issued to George A. M. Butterworth et al.; 3,976,074 issued to Harry G. Fitzgerald et al.; 4,054,141 issued to Julius Schwaiger et al.; 4,047,531 issued to Hamzeh Karami; 3,545,441 issued to Gunnar Gravdahl and 4,219,024 issued to Donald Patience et al.

The prior art listed above recognizes the desirability of having a capillary gradient with larger capillaries nearest the body of the wearer and smaller capillaries in the area where maximum absorbency is desired. If the absorbent matrix in the napkin was designed so that the smallest capillaries were closest to the body of the wearer, fluid would remain in the area of the smallest capillaries and would not disperse through the rest of the absorbent matrix due to capillary attraction. If a number of large capillaries are near the point of fluid contact and a greater number of small capillaries are farther from that point, then fluid will be drawn away from the initial contact site.

In general, the greater the level of unfused thermoplastic material, the higher the amount of shape recovery introduced into the absorbent matrix of the sanitary napkin.

A napkin with a relatively thick layer of large capillaries readily transfers relatively low viscosity fluids such as urine, water, or even blood. It has been recognized, however, that menses is a complex fluid with uterine blood being only one component of its composition. Additionally, menses contains cellular debris and a mucus-like fraction. It has also been recognized that the character of menses can differ in composition, viscosity, volume and flow rate from individual to individual and also at different times in the menstrual cycle with a given individual. It has also been determined that certain women have consistently high viscosity menses and comparatively low flow volumes.

Since highly viscous menses has been identified, it has now been discovered that the composition of menses also has a significant effect on the transport of fluid from the cover into the absorbent matrix of a sanitary napkin. When the viscosity and cellular debris content of menses are relatively low, usually during periods of high flow, it passes relatively rapidly through the cover material and into the absorbent matrix; even in cases where the portion of the absorbent matrix adjacent the cover material has relatively large capillaries. However, it has been observed that more viscous, high debris-content menses, especially prevalent during periods of low flow, tends to stay on the upper surface of the cover. In addition, particularly when there is little capillary attractive force exerted on the bottom of the cover by the absorbent matrix, the fluid component tends to stay on the surface and then run off the sides of the napkin. It is believed that earlier attempts at designing sanitary napkins containing thermoplastic materials have been unsuccessful because of the failure of the absorbent matrix to draw viscous menses through the cover material.

U.S. Pat. Nos. 4,214,582 issued to Harish A. Patel and 3,285,245 issued to Charles L. Eldredge et al describe wound dressings in which a thermoplastic fluid pervious cover is fused to an absorbent layer also containing thermoplastic. The Patel patent discloses a wound dressing having a hydrophobic cover, a microcreped absorbent layer underneath the cover and a second hydrophobic cover positioned on the bottom of the absorptive layer. This combination is subjected to embossing by a compactor to provide large locally fused discrete portions along the cover surface in contact with the wound. This relatively severe compression in fusing is designed to provide an irregular top surface for ease of release from the wound area as it heals. The fusing of the major proportion of the top surface area also provides a suitable release surface.

The Eldredge patent discloses a surface in which the fusible fibers are drawn through the cover material to provide a soft matt finish and aid in the wicking of fluid wound exudate along the top surface of the cover and into the main absorbent area through the cover.

Neither of these configurations would be particularly useful for a sanitary napkin. In the wound dressing described by Patel, the rapid discharge of fluid would settle on the relatively large fused surface since there is no penetration of fluid in the fused area. The relatively great amount of compression applied over relatively substantial areas in Patel also tends to destroy such deformability and compressibility as may otherwise have been present. To design a napkin having the Eldredge configuration would tend to provide a competing capillary structure above the cover which would tend to trap debris and prevent fluid transfer into the napkin resulting in a perpetually wet surface after initial discharage.

SUMMARY OF THE INVENTION

According to this invention the sanitary napkin is provided with improved comfort and the ability to relatively rapidly transfer viscous menses from the cover into the absorbent matrix. The absorbent matrix contains principal absorbent component characterized by relatively high fluid retention and a second component including comfort enhancement capabilities positioned at least in part between the principal absorbent and the fluid permeable cover or wrap. The second component is integrated with the cover to provide intimate contact and densification of localized regions. As a consequence, fluid transfer routes are established and fluid is conveyed to the principal absorbent component.

When used in this specification, a comfort enhancement layer may include the entire layer which in certain configurations extends around the sides and at least a part of the bottom of the principal absorbent component layer while the fluid transfer layer terminology refers only to the position of the comfort enhancement layer between the top of the cover and the absorbent on the body facing side.

BRIEF DESCRIPTION OF THE DRAWINGS

The invention may be more readily understood by reference to the drawings in which.

DETAILED DESCRIPTION OF THE INVENTION

Figure 1:
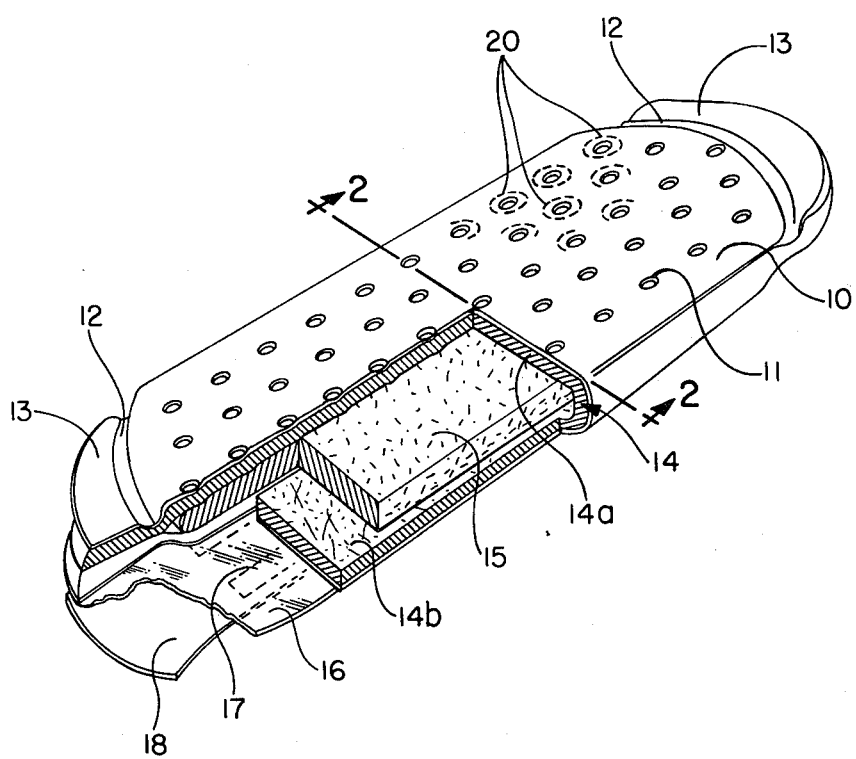
FIG. 1 is a perspective view partially in cross section of one embodiment of the sanitary napkin of this invention.
Figure 2:
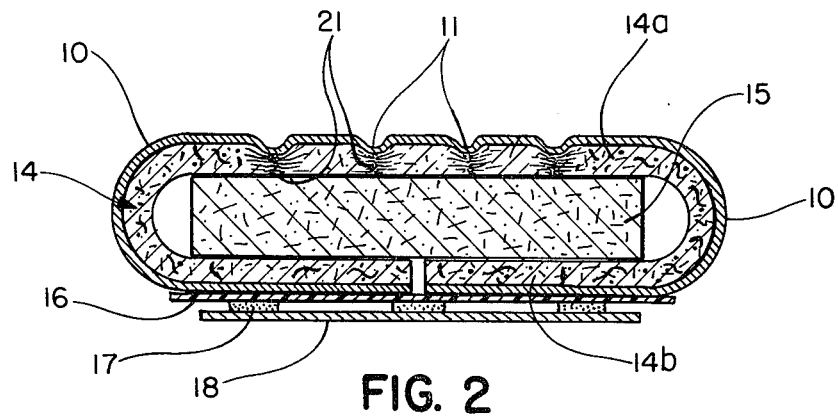
FIG. 2 is a cross sectional view taken along lines 2—2 of FIG. 1.

According to the embodiment shown in FIGS. 1 and 2 a sanitary napkin is provided having a fluid pervious cover 10 and a thermoplastic-containing comfort enhancing layer 14 which surrounds an absorbent layer 15. The comfort enhancement layer 14 has a bottom portion 14b to further improve comfort and a top portion 14a. Attached to the bottom portion 14b is a fluid impermeable baffle 16. Garment suspension adhesive lines 17 are centrally longitudinally positioned on baffle 16 and a release liner 18 is removably attached to the bottom surface of the adhesive lines 17. The comfort enhancing layer 14 is preferably coextensive with the cover 10 at the ends of the napkin 13 which are sealed, e.g., by ultrasonic bonding as shown by fused lines 12 which are inset from the ends 13.

The outer wrap or cover is integrated to the comfort enhancement layer 14 at least at selected parts of the transfer layer 14a corresponding to integration sites 11 of the wrap 10. Integration refers to the bonding of the wrap 10 to at least the transfer layer 14a at sites 11 at distances not greater than 2 centimeters apart at least in the perineal area of the napkin.

The perineal area of the napkin is that portion of the napkin abutting the perineal area of the wearer. This portion, depending on the design of the napkin and the positioning of the napkin by the wearer, is generally centered longitudinally and transversely and is 1 centimeter wide in the transverse direction and 5 centimeters long. As will become apparent, it is desirable that at least one and preferably at least 2 to 3 integration sites be present at the napkin surface directly beneath the perineal area of the wearer.

Integration may occur throughout the top of the cover and may be used to bond the layer 14 to the cover 10 which may then be treated as a single unit for manufacturing purposes and this is desirable for ease of processing.

Bonding to accomplish integration can be by the application of heat, such as by hot calender embossing, or by ultrasonic means or it can be by mechanical manipulation of fibers with or without heat as, in needling. It is preferred that bonding be by heating means and ultrasonic bonding is particularly preferred. The bonding, if by heat may be something less than fusing such as described in U.S. Pat. No. 3,855,046.

The bonding step may, in fact, produce holes in the cover material itself which may extend into the comfort enhancement layer depending upon the severity of the bonding treatment. It is also possible that stray fibers may penetrate the cover 10 on occasion and penetration may occur at or near the area of integration. Large amounts of this penetration is undesirable however, because the body-facing surface of the cover must be as dry as possible. If large amounts of fiber are present, particularly if this fiber is contiguous over an area, lateral surface wicking occurs and the surface produces a highly objectionable wet tactile sensation which is likely to result in the premature discarding of the napkin. Integration of the cover 10 to the transfer layer 14a of the comfort enhancement 14 alters the character of the transfer portion 14a by providing transfer zones 21 of increased density and compression which diminish as they extend radially outwardly from the integration sites 11 through the depth of the transfer portion 14a. It should be noted that the part of layer 14a directly under the integration sites may be entirely fused and not form part of zone 21.

These zones 21 which are observable and quantifiable by microscopic examination as to their extent and degree of compaction provide conduits for transfer of viscous menses described previously. Transfer occurs in these zones 21 where the capillaries are predominantly not greater in size than that of the absorbent layer 15.

Transfer areas 20, illustrated by dotted lines in FIG. 1, are areas which are directly above the transfer zones 21 and indicate the portion of the cover where fluid transfer will first occur from the top of the cover through the layer 14a. These transfer areas 20 vary from being irregular to circular in shape, and may overlap. There may be portions of the surface of the napkin which are neither integration sites 11 nor transfer areas 20. These areas lack capillary attractive force to pull fluid through and for that reason, transfer of viscous, cellular debris and mucoid-containing menses through this portion of the surface of the napkin is extremely slow if it occurs at all. Relatively nonviscous fluid will transfer downward more readily through these portions but will preferentially transfer in the transfer areas 20. These portions which are neither transfer zones or bond sites in the transfer layer 14a help provide the comfort enhancement features of the napkin of this invention.

The reason for having integration sites with the resultant transfer areas 20 and transfer zones 21 beneath the areas of fluid discharge becomes readily apparent with these facts in mind. It has been found that viscous menses of the type previously described transfers when as little as 0.12% of perineal area of the napkin beneath the body of the wearer is transfer area.

This minimal amount of transfer area can be obtained by positioning a single integration site in the 1 by 5 cm perineal area.

The effect of integration, with regard to the number and size of the integration sites in this 1 by 5 cm area is also important. Fluid transfer seldom if ever occurs through the integration site. Large integration sites, contiguous integration sites and several closely spaced integration sites are therefore to be avoided particularly when integration is by fusing. It is generally preferred to maintain individual integration sites more than 0.15 centimeters apart, in any event, because the higher the level of integration the stiffer and therefore the less comfortable the napkin becomes. It has been found that when the fused bond sites are more than 20% of the 1 by 5 cm area on the surface of the integrated cover where fluid transfer occurs, there is significant puddling of menses rendering the napkin unsuitable for use. It is preferred that if fusing is utilized as the process for integration, the fused area is less than 10% and particularly between 0.5 and 5% of the napkin cover surface.

Since it is preferred that the transfer layer 14a be integrated with the cover 10 prior to napkin assembly it is easiest to maintain the same integration pattern with regard to spacing over the entire surface 14a as well as layer 14b. From the standpoint of fluid transfer, into layers 14a and 15, however, it is apparent that the critical portion for control of transfer area and integration is that part of the napkin surface directly under and nearest initial fluid discharge, i.e., the perineal area of the napkin defined earlier.

It has been observed that fusing of the comfort enhancing layer 14 particularly at fluid transfer layer 14a prior to integration with the cover 10 increases the efficiency of viscous menses transfer possibly by increasing the number of small capillaries around the integration sites 11. However, fusing tends to stiffen the layer and, therefore a tradeoff of benefits results. It should be noted that the minimum transfer area described above is based upon the use of a fused transfer layer 14a. Fusing as defined herein is the partial softening and/or melting of a thermoplastic material to provide bonds with the thermoplastic.

The transfer layer may contain nonthermoplastic fibers, absorbent fibers such as rayon, superabsorbent rayon, cellulosic fibers or blends of the above.

Suitable thermoplastic fibers are polyester, polypropylene, acrylic or nylon fibers or blends. Crimped fibers add comfort and their use at least at some level is preferred.

If fusing is desired the addition of a low melting point readily fusible fiber is highly desirable. Suitable fusible fibers for this invention are: Vinyon, a vinyl chloride/vinyl acetate copolymer sold by Avtex Fibers Inc. of New York, N.Y.; Eastman 410 amorphous or crystalline polyester fibers sold by Eastman Chemical Products, Inc., a Subsidiary of Eastman Kodak Co., Kingsport, Tenn.; or Chisso ES a bicomponent polypropylene/polyethylene fiber sold by Chisso Ltd., Osaka, Japan, which due to its differential melting point for each component of the fiber, could be used as the only thermoplastic fiber as well as in blends with other fibers.

The comfort enhancing layer can be formed by carding or it may be airlaid, however, randomized carding is preferred because it increases bulk and therefore perceived dry softness to the comfort enhancing layer.

The transfer layer 14a has a basis weight range from 30 to 400 gms/square meter and a thickness generally between about 0.1 to about 1 cm. Of course, if the embodiment depicted, for example at FIGS. 1 and 2 is used, there will be two layers 14a and 14b each having thickness and basis weight characteristics within the parameters set forth above. These values may not be identical for layers 14a and 14b however if only the transfer layer 14a is integrated.

The cover or outer wrap 10 of the napkin of this invention is primarily of a nonwoven thermoplastic web and should be of a sufficiently open structure to enchance the transfer of the viscous fluid menses described above into the transfer layer 14a.

For a cover to readily transfer this viscous fluid according to the teachings of this invention it must be sufficiently open to enhance transfer. While the surface of the cover may be altered by treatment with suitable surface active agents, to aid in the transfer certain cover structures have been found to perform better than others and their performance has been correlated to the number of small holes present.

Several cover materials were submitted for examination by a Quantimet 900 Image Analyzer made by Cambridge-Imanco Ltd, Cambridge, England. A Bausch and Lomb Model L transmitted light photomicrographic unit was employed to take photomicrographs of cover materials which had been previously tested. The photomicrographs were examined with the Image Analyzer pixel size set at 13.28 microns.

For a cover to be acceptable no more than 40% of the holes or pores may have a breadth of less than 27.3 microns; with preferred covers having less than 25% of the holes which are less than 27.3 microns. Breadth is defined as the maximum dimension of the hole measured at 90° to the major axis of the hole.

A second set of measurements which were taken directly on the cover material with a pixel size of 3.04 microns revealed that preferred cover materials should have no more than 90 holes/mm$^2$ with a breadth of less than 13 microns. Generally, this latter breadth measurement has been correlated to fluid retention within the cover. In other words, a potential cover material may transfer fluid but retain a significant amount within the cover holes, thus producing a wet feeling surface.

One of the thermoplastic nonwoven cover materials which meets the first criterion and is acceptable is Sharnet (x1008-30A). Sharnet is a trademark of Inmont Corp., Somerville, Mass.

A most preferred cover material which meets both criteria is a uniform spunbonded nonwoven web having 3 denier or larger filaments. Such a material is described in copending patent application bearing Ser. No. 146,450 filed May 5, 1980 by Appel and Morman which has been informally allowed and is hereby incorporated by reference.

EXAMPLE I

Comfort enhancement as used herein relates to the force needed to compress the cover and the absorbent matrix, i.e., the transfer layer integrated with the cover layer and the principal absorbent layer. For purposes of this invention a standard wood pulp fluff layer was used as indicated below as the principal absorbent layer. This fluff was fiberized in a hammermill and has a basis weight of 580 gm/m$^2$ which is a value between that of the standard commercial fluff used for maxi pads and that used for mini pads sold under the NEW FREEDOM trademark by Kimberly-Clark Corporation of Neenah, Wis. Several 3×6 in. fluff blanks were prepared. Several 3×3 in. samples of both fused and unfused transfer layers having differing degrees of integration were also prepared and centered on the fluff.

The test described below was run on an Instron Model TM with an integrator unit Model DI-53 with a compression load cell model CC having a 2¼ in. diameter compression ram.

The transfer layer basis weight used for all samples was 0.0129 g/cm². The preferred cover described earlier of a uniform spunbonded polypropylene web having 3 denier filaments was integrated to several samples of the transfer layer by ultrasonic bonding with a 0.078 cm diameter pin with the spacing between integration for each sample indicated in the table below. (This pin value is ±0.01 cm due to wear encountered on the pin head.) A glycerol water mixture having a viscosity of 700 centipoises at 21° C. and a surface tension of 52±2 dynes/cm was prepared. Pluronic F68 a surfactant made by Wyandotte Chemical Corporation, Wyandotte, Mich., a division of BASF was used to obtain the desired surface tension and a red dye was added. This fluid has proven to be a satisfactory simulation for the fluid transfer characteristics of the viscous menses described throughout this disclosure. Ten ccs of this fluid are added through a ¾ inch diameter orifice in a plexiglass block weighing 113.3 gm. The block rested on each sample with a 2 in. diameter circular base with the orifice centered. After all of the fluid enters the cover the block is removed without exerting downward pressure. The sample is allowed to sit for 5 minutes. Each of the samples was wrapped in 5 by 8 in. sheets of 2 mil-polyethylene film.

The sample is centered under a 2¼ in. diameter circular Instron ram head. The Instron and Integrator was calibrated as per standard procedure and the cross head speed set to 2 in./min. Each sample was individually compressed to 40% of the original dry thickness as measured on Custom Scientific Instruments Thickness Tester Model CS-55-210.

As compression occured the force applied to compress and the distance the ram head travels was recorded. After compression was accomplished the force was removed by reversing ram head direction at the same cross speed thereby providing a recovery period. The cycle of compression and recovery was repeated an additional 9 times to obtain an equilibrium state for each sample tested.

The maximum force ($F_{max}$) exerted during the equilibrium cycle is representative of the condition of the napkin which has been compressed during use. According to this test, comparatively lower values are better because they reflect comfort as a function of residual wet compressibility.

TABLE 1

| | $F_{max}$ 60% Compression (gms) | |
|---|---|---|
| Bond Spacing (cm) | With Fused Transfer Layer | With Unfused Transfer Layer |
| 0.251 | 6810 | 7470 |
| 0.359 | 7730 | 5960 |
| 0.539 | 6010 | 6520 |
| 0.718 | 6869 | 4710 |
| 0.898 | 4831 | 4210 |
| 1.796 | 3451 | 2840 |

For comparison a napkin blank with fluff only was tested and yielded a value of 8610 gms. The addition of conventional cover materials does not significantly alter this value. Values greater than 7000 gms are not desirable.

EXAMPLE II

During the test performed to produce the data set forth in Example I the Instron data were evaluated at the 50% compression points on the first and the last, i.e., equilibrium cycles. The ratio between the forces at 50% compression is a measure of the resistance of the pad to permanent distortion, $F_1$ being the value of the force at the initial 50% compression cycle and $F_{eq}$ the value of the force applied at the equilibrium, i.e., tenth compression cycle.

TABLE 2

| | Ratio of $F_{eq}/F_1$ | |
|---|---|---|
| Bond Spacing cm. | Fused | Unfused |
| 0.251 | 0.171 | 0.178 |
| 0.359 | 0.186 | 0.159 |
| 0.539 | 0.237 | 0.210 |
| 0.718 | 0.245 | 0.207 |
| 0.898 | 0.344 | 0.235 |
| 1.796 | 0.320 | 0.345 |

For comparison purposes fluff only had a value of 0.068 and when conventional cover materials were placed over the fluff no significant change was observed when compared to the fluff alone.

It should be noted that values greater than 1/10 are desirable and especially preferred are values greater than 1/5. The greater this ratio the less the change in a wet pad during use.

Since in all instances in the above examples the bond points were arranged in square patterns, the amount of fused area can be determined by calculating the area of the embossing pins contacting the surface. In the case of the closest spacing set forth, assuming the maximum possible number of fused sites within the perineal area of the napkin, the amount of fused area is about 9.6% with the variance again due to variability in pin head diameter. This particular configuration has lost a substantial amount of comfort and softness when compared to the wider spacing set forth in the Table above and from the standpoint of increased tactile satisfaction by the wearer, this number provides a realistic maximum.

The principal absorbent layer 15 may be any conventional absorbent used in feminine protection products such as cellulosic fibers or the like and may contain absorbency additives, e.g., superabsorbents. One useful material for the principal absorbent 15 is described in U.S. Pat. No. 4,100,324. This material is a turbulently conformed mixture of airlaid meltblown microfibers and a cellulosic material such as wood pulp fluff. The absorbent activity may be heightened by the addition of absorptive materials having higher absorptive capacity per unit weight and these materials such as superabsorbent materials may be used as the primary absorbent to the exclusion of, or in conjunction with conventional cellulosic absorbents within the scope of this invention.

Figure 3:
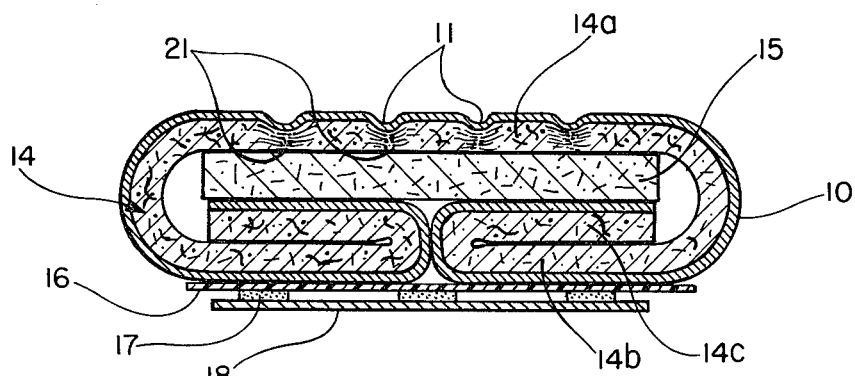
FIG. 3 is a cross section of a second embodiment of the construction of the sanitary napkin according to this invention.

The embodiment depicted in FIG. 3 is identical to that in FIGS. 1 and 2 except that the absorbent portion containing the thermoplastic 14 along with the cover 10 is folded onto itself on the bottom of the absorbent area at 14c to provide additional comfort enhancement. The garment attachment adhesive 17 is shown attached to the baffle 16 outside of the cover wrap 10. A release liner 18 is conventionally provided to protect the attachment adhesive. Extra comfort enhancement layers can be added under the fluff and, in fact, a series of coterminous comfort enhancement layers may be used. These layers can also be coterminous with the principal absorbent layer within the scope of this invention.

Figure 4:
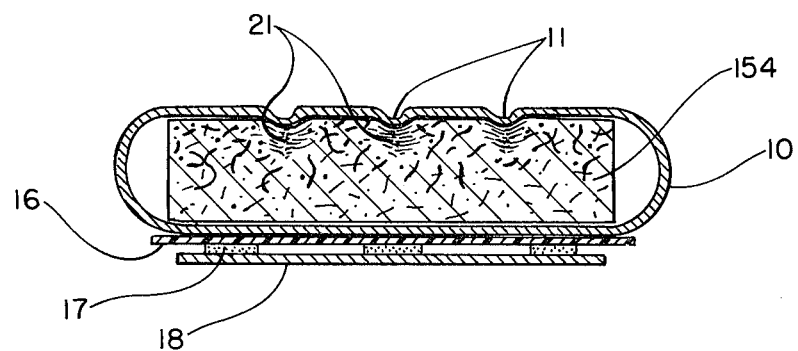
FIG. 4 is a cross section of a third embodiment of the sanitary napkin according to this invention. In all figures like numbers relate to like portions.

FIG. 4 illustrates an embodiment which is different than the other two embodiments because, in this instance, the thermoplastic is present in the same layer as the conventional absorbent portion 154 but is present in a higher percentage near the body facing surface of the napkin. Although the currently preferred embodiments are those depicted in FIGS. 1, 2 and 3 because of the simplicity of manufacture this embodiment is also contemplated by this invention.

What is claimed is:

1. A sanitary napkin with a perineal area generally corresponding to and positioned beneath the perineal area of the wearer in use comprising:
   (a) a fluid permeable cover with a body contacting surface;
   (b) an absorbent matrix system including a principal absorbent portion and a transfer portion including thermoplastic material;
   (c) said transfer portion positioned between said cover and said principal absorbent portion and in fluid conductive contact between said cover and said principal absorbent portion and integrated at spaced apart sites with said cover, at least in the perineal area, to produce zones of greater density and enhanced fluid conduction relative to the remainder of said transfer portion; said zones corresponding to a transfer area on said cover, said transfer area being not less than 0.12% of said napkin perineal area; and
   (d) a fluid impermeable baffle adjacent said absorbent matrix system having a garment facing surface and an absorbent-matrix-system-facing-surface.

2. A sanitary napkin characterized by relatively improved comfort as measured by reduced wet compressibility with a perineal area generally corresponding to the perineal area of the wearer in use comprising:
   (a) a fluid permeable cover with a body contacting surface;
   (b) an absorbent matrix system including a principal absorbent portion and a transfer portion including thermoplastic material;
   (c) said transfer portion positioned between said cover and said principal absorbent portion and in fluid conductive contact between said cover and said principal absorbent portion and integrated at spaced apart sites with said cover, at least in the perineal area, to produce zones of greater density and enhanced fluid conduction relative to the remainder of said transfer portion; said zones corresponding to a transfer area on said cover;
   (d) a fluid impermeable baffle adjacent said absorbent matrix system having a garment facing surface and an absorbent-matrix-system-facing-surface; and
   (e) said wet compressibility being defined as an $F_{max}$ at 60% compression of not greater than 7000 gms when said wet compressibility is measured for said matrix system based upon a principal absorbent layer of wood pulp fluff having a basis weight of 580 gm/m$^2$.

3. A sanitary napkin having relatively increased resistance to permanent distortion with a perineal area generally corresponding to and positioned beneath the perineal area of the wearer in use comprising:
   (a) a fluid permeable cover with a body contacting surface;
   (b) an absorbent matrix system including a principal absorbent portion and a transfer portion including thermoplastic material;
   (c) said transfer portion positioned between said cover and said principal absorbent portion and in fluid conductive contact between said cover and said principal absorbent portion and integrated at spaced apart sites with said cover, at least in the perineal area, to produce zones of greater density and enhanced fluid conduction relative to the remainder of said transfer portion; said zones corresponding to a transfer area on said cover;
   (d) a fluid impermeable baffle adjacent said absorbent matrix system having a garment facing surface and an absorbent-matrix-system-facing-surface; and
   (e) said increased resistance to permanent distortion being measured when the principal absorbent layer is wood pulp fluff having a basis weight of 580 gm/m$^2$ and when the ratio $F_{eq}/F_1$ is at least 1/10 at 50% compression.

4. A sanitary napkin according to claim 1, 2, or 3 wherein said transfer portion is coterminous with said cover and integrated thoughout the coterminous surfaces.

5. A sanitary napkin according to claim 1 wherein integration occurs at sites between at least 0.75 and 2 centimeters apart.

6. The napkin according to claim 3 wherein the $F_{eq}/F_1$ is at least 1/5 at 50% compression.

7. The napkin according to claim 1 wherein the principal absorbent layer is a coformed airlaid mixture of meltblown thermoplastic and cellulosic fibers.

8. The napkin according to claim 1, 2 or 3 wherein the transfer portion is a separate part of a comfort enhancement layer, said comfort enhancement layer extending around the side edges and at least a part of the surface of the principal absorbent portion opposite the surface in fluid conductive contact with the transfer portion.

9. The napkin according to claim 1, 2, or 3 wherein the transfer portion is a separate part of a comfort enhancement layer and extends around the side edges of the napkin and is folded in a double thickness at the surface of the principal absorbent portion opposite the surface in fluid conductive contact with the transfer portion.

10. The napkin according to claim 1, 2, or 3 wherein the transfer portion contains between about 40 and about 100% by weight of thermoplastic material.

11. The napkin according to claim 1, 2, or 3 wherein the principal absorbent layer is primarily cellulosic material.

12. The napkin according to claim 1, 2, or 3 wherein the absorbent matrix is formed as a unitary layer having thermoplastic material with higher levels of thermoplastic present in at least that part of the absorbent matrix adjacent the cover.

13. The napkin according to claim 1, 2, or 3 wherein integration is not greater than 20% of the perineal area of the napkin.

14. The napkin according to claim 1, 2, or 3 wherein integration is not greater than 10% in the perineal area of the napkin.

15. The napkin according to claim 1, 2, or 3 wherein integration is between 0.5 and 5% in the perineal area of the napkin.

16. The napkin according to claim 1, 2, or 3 wherein the cover material has no greater than 40% of its pores with a breadth of less than 27.3 microns.

17. The napkin according to claim 1, 2, or 3 wherein the cover material has no greater than 40% of its pores with a breadth of less than 27.3 microns and no greater than 90 pores/mm$^2$ with a breadth of less than 13 microns.

18. The napkin according to claim 1, 2, or 3 having a plurality of mutually coterminous layers at least one of which is a principal absorbent layer.

19. The napkin according to claim 1, 2, or 3 having a plurality of coterminous comfort enhancement layers.

* * * * *

UNITED STATES PATENT AND TRADEMARK OFFICE
CERTIFICATE OF CORRECTION

PATENT NO. : 4,397,644
DATED : August 9, 1983
INVENTOR(S) : Billie J. Matthews, John P. Allison, Paul S. Woon, Robert A. Stevens, Stephan R. Bornslaeger It is certified that error appears in the above-identified patent and that said Letters Patent are hereby corrected as shown below:

Column 7, line 65, "6869" should be changed to --5869--.

*Signed and Sealed this*

*Thirty-first* Day of *January 1984*

[SEAL]

*Attest:*

GERALD J. MOSSINGHOFF

*Attesting Officer*   *Commissioner of Patents and Trademarks*